United States Patent [19]

Hardtmann

[11] 4,032,528

[45] June 28, 1977

[54] 1,4-SUBSTITUTED-QUINOLIN-2(1H)-ONES AS CNS AGENTS

[75] Inventor: Goetz E. Hardtmann, Morristown, N.J.

[73] Assignee: Sandoz, Inc., E. Hanover, N.J.

[22] Filed: Sept. 18, 1975

[21] Appl. No.: 614,377

Related U.S. Application Data

[63] Continuation-in-part of Ser. No. 454,070, March 25, 1974, abandoned, which is a continuation-in-part of Ser. No. 303,099, Nov. 2, 1972, abandoned, and Ser. No. 392,082, Aug. 27, 1973, abandoned.

[52] U.S. Cl. .............................. 260/289 R; 424/258
[51] Int. Cl.$^2$ ........................................ A61K 31/47
[58] Field of Search ................. 260/289 R; 424/258

[56] References Cited

FOREIGN PATENTS OR APPLICATIONS 3,694M  11/1965  France

*Primary Examiner*—Stanley J. Friedman
*Attorney, Agent, or Firm*—Gerald D. Sharkin; Richard E. Vila

[57] ABSTRACT

Disclosed are compounds which are 1-alkyl-4-alkoxyquinolin-2(1H)-ones, e.g., 1-methyl-4-butoxyquinolin-2(1H)-one, and which are useful as CNS depressant agents. The compounds may be prepared, for example, by reacting a 1-alkyl-4-hydroxyquinolin-2(1H)-one with an alkyl halide in presence of base.

4 Claims, No Drawings

1,4-SUBSTITUTED-QUINOLIN-2(1H)-ONES AS CNS AGENTS

DISCLOSURE OF INVENTION

This application is a continuation-in-part of application Ser. No. 454,070, filed Mar. 25, 1974, which is a continuation-in-part of application Ser. No. 303,099, filed Nov. 2, 1972, and of application Ser. No. 392,082, filed Aug. 27, 1973, all are now abandoned.

The present invention relates to chemical compounds and their use as pharmaceutical agents, and more particularly to compounds which are 1-alkyl-4-alkoxyquinolin-2(1H)-ones and their use as CNS depressants, e.g., tranquillizer and anti-convulsant agents.

The compound which is 1-methyl-4-methoxyquinolin-2(1H)-one is known from Lamberton et al., Australian J. Chem. 6, 173–9 (1953) and from McCorkindale, Tetrahedron, 1961, Vol. 14, pp. 223–229. It has been now found that 1-methyl-4-($C_4$–$C_6$)alkoxyquinolin-2(1H)-ones form a series of compounds having strong CNS activity, i.e., tranquillizer and anticonvulsant activity.

The compounds which are the subject of the present invention may be represented by the following structural formula I:

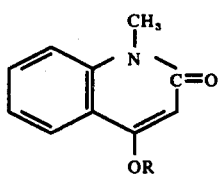

wherein R is alkyl of 4 to 6 carbon atoms, preferably straight chain alkyl of 4 or 5 carbon atoms.

The compounds I may be prepared in a Step A reaction by reacting a compound of the formula II:

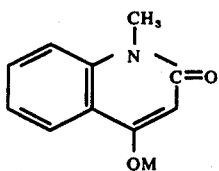

wherein M is hydrogen or an alkali metal, with a compound of the formula III:

RX      III wherein R is as defined and X is chloro, bromo or iodo or a radical of the formula IIIa:

BO-      IIIa in which B is methanesulfonyl, benzenesulfonyl or p-toluenesulfonyl.

The preparation of compounds I by the reaction of Step A may be suitably carried out at temperatures of from 0° C. to 120° C., preferably 10° C. to 40° C. The reaction may be carried out in absence of added solvent when III is liquid but is preferably effected with an inert solvent of conventional type such as dioxane, dimethylformamide and dimethylacetamide. The compounds of the formula II in which M is an alkali metal are preferably employed and are formed in a conventional manner by reacting a compound II in which M is hydrogen with a strong base such as an alkali metal hydride, an alkali metal hydroxide or alkali metal carbonate, preferably sodium hydride. When Step A is carried out employing a compound II in which M is hydrogen it is desirable to effect the reaction in the presence of strong base such as an alkali metal hydride, e.g., sodium hydride, or an alkali metal carbonate, e.g., potassium carbonate, and preferably at temperatures of from 10° C. to 80° C. The reaction product of the formula I may be recovered from the reaction mixture of Step A by working up by established procedures.

The compounds of the formula I may also be prepared in process B by reacting a compound of the formula IV:

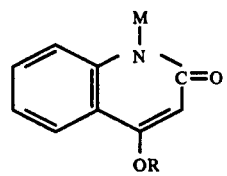

wherein R and M are as above defined, with a compound of the formula V:

$CH_3X$      V wherein X is as defined above.

The preparation of compounds I by the reaction of process B may be suitably carried out at temperatures of from 0° C. to 120° C., preferably 10° C. to 40° C. The reaction may be carried out in absence of added solvent when V is liquid but is preferably effected with an inert solvent of conventional type such as dioxane, dimethylformamide and dimethylacetamide. The compound of the formula IV in which M is an alkali metal are preferably employed and are formed in a conventional manner by reacting a compound IV in which M is hydrogen with a strong base such as an alkali metal hydride, an alkali metal hydroxide or alkali metal carbonate, preferably sodium hydride, at temperatures of from 0° C. to 120° C., preferably 10° C. to 80° C. When process B is carried out employing a compound IV in which M is hydrogen it is effected in the presence of a strong base such as an alkali metal hydride or carbonate, e.g., sodium hydride or potassium carbonate, and at temperatures of from 0° C. to 120° C., preferably 10° C. to 80° C. The reaction product of the formula I may be recovered from the reaction mixture of process B by working up by established procedures.

The compound of the formula II in which M is hydrogen is known, for example, from U.S.Pat. No. 3,133,928 in which said type of compound is disclosed and depicted in the alternative or tautomeric form having the structural formula IIa:

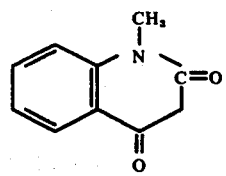

The compounds of the formula IV employed in process B may be prepared by subjecting a compound of the formula IVa:

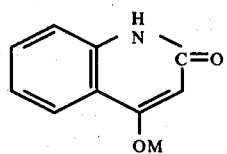

IVa wherein M is as defined, to reaction analogously to that of processes A and B as described above using controls to avoid any substantial alkylation of the 1-position of said compound IVa. Such control may be effected in the reaction in which the strong base is employed by: (1) employing no more than about the theoretical amount of sodium hydride or other base used in the reaction, or (2) by empliying a base to compound IVa mol ratio of about 1.5 to 1 or more and temperatures within the range of from 0° C. to 40° C., preferably 15° C. to 30° C., with the time and temperature of the reaction being regulated inversely with the mol ratio of base to compound IVa. In general, the mol ratio of base relative to the compound IVa is desirably no more than 3.1. Preferably, the ratio is about 1:1 and the temperature from 15° C. to 30° C.

The compound of the formulae IV and IVa in which M is hydrogen are either known or may be prepared from material by the known procedures.

The compound of the formula IIaa:

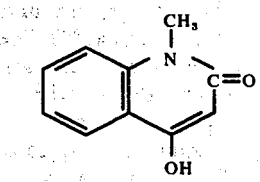

IIaa may also be produced by hydrolysis and decarboxylation of a compound of the formula VI:

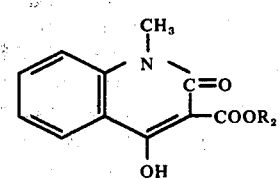

VI in which $R_2$ is alkyl of 1 to 4 carbon atoms.

The hydrolysis may suitably be effected in the presence of a strong base, e.g., sodium hydroxide in an aqueous medium, e.g., water or aqueous ethanol, and at a temperature of from 40° C. to 150° C., preferably 80° C. to 120° C. The mixture may suitably then be acidified with, for example, hydrochloric acid, and at a temperature of from 0° C. to 150° C., preferably 10° C. to 50° C., whereupon the free acid decarboxylates to yield the desired product. Where $R_2$ signifies t-butyl, the process is more suitably effected at a temperature of from 80° C. to 250° C., preferably 130 C. to 200° C. and in the presence or absence of an added solvent, such as a hydrocarbon or chlorinated hydrocarbon solvent.

The resulting compounds of formula IIaa may be isolated and purified using conventional techniques.

The compounds of formula VI are novel and may be produced by reacting the compound of formula VII:

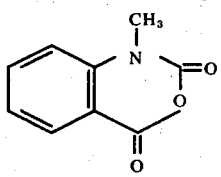

VII with a compound of formula VIII:

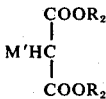

VIII in which $R_2$ is as defined above, and

M' signifies an alkali metal.

The process is suitably carried out in an inert organic solvent, e.g., dimethyl acetamide, and at a temperature of from 0° C. to 150° C., preferably 60° C. to 120° C. followed, if necessary, by neutral or acid hydrolysis to obtain the desired compound VI from any 4-alkali metal salt thereof initially produced.

The compounds of formula VIII may be produced from the corresponding dialkyl malonates by reaction with a strong alkali metal base, e.g., sodium hydride, and in an inert organic solvent, e.g., dimethyl acetamide.

The resulting compounds of formula VI may be isolated and purified using conventional techniques.

The compounds of formula VII are either known or may be produced in conventional manner from available materials.

The compounds of the formula I are useful because they possess pharmacological activity in animals. In general, the compounds I effect a depression of the central nervous system and are useful as minor tranquilizers and anti-convulsants as indicated by a CNS depressant (docility) effect in behavior tests in mice 12–200 mg./kg.) and by an inhibition of chemically induced seizures in mice on intraperitoneal administration (10–100 mg./kg.) using 50 mg./kg. of N-sulfamoylazepine to induce seizures. The compounds I also effect a reinduction of hexobarbital anesthesia in mice (10–200 mg./kg.). Certain of the compounds I (R being $C_4$ or $C_5$ straight chain alkyl) such as those of Examples 1 and 2d hereinafter, in addition to all the above indications, produce a neurological deficit and muscle relaxation in the "rotarod test" in mice on administration intraperitoneally (10–150 mg./kg.) essentially according to the method of Dunham et al., J. Am. Pharm. Assoc. 45:208 1957, and/or a depression of spiral reflexes in anesthetized male cats on intravenous administration (0.5–20 mg./kg.) as determined by measuring flexor and patellar responses using force displacement transducers. The compound which is 1-methyl-4-butoxyquinolin-2(1H)-one also inhibits aggression in the shocked-induced fighting mice test on administration intraperitoneally (20–100 mg.kg.), but has not been found to give positive results in the Thalamond rigity test.

For the above-mentioned usage, the dosage administered will, of course, vary depending upon known factors such as the compound used, mode of administration and therapy desired. However, in general, satisfactory results for the tranquilizer usage may be obtained on administration at a daily dose of from about 1.2 to 200 milligrams per kilogram of body weight, preferably given orally and in divided doses 2 to 4 times a day or in sustained release form. For larger mammals the administration of from 80 milligrams to 2000 milligrams of the compound per day provides satisfactory results and dosage forms suitable for internal administration comprise from about 20 milligrams to about 1000 milligrams of the compound in admixture with a solid or liquid pharmaceutical carrier. For anti-convulsant use, satisfactory results are obtained on the daily administration of from 1.0 to 100 milligrams per kilogram, preferably given orally and in divided doses of sustained release form, the amount per day for larger mammals being 60 to 1000 milligrams in dosage forms comprising 15 to 500 milligrams.

For the above usage, the compounds of the formula (I) are preferably combined with one or more conventional pharmaceutically acceptable carriers, and such other conventional adjuvants as may be desired or necessary, and the resulting composition administered orally in such forms as tablets, capsules, granules, dispersible powders, elixirs, syrups, suspensions and the like or parenterally in the form of an injectable solution, suspension or the like, e.g., a sterile injectable aqueous suspension. Such compositions may be prepared according to any method known in the art for the manufacture of pharmaceutical compositions. In general, the compositions of the invention adapted for either oral or parenteral administration may contain 1% to 90% by weight of the active ingredient in combination with the inert carrier, more usually 3% to 40%.

The preferred pharmaceutical compositions from the standpoint of preparation and ease of administration are solid compositions, particularly hard-filled capsules and tablets.

Tablets and capsules containing the ingredients indicated below may be prepared by conventional techniques and are useful in effecting tranquillization and an inhibition of convulsions at a dose of one tablet or capsule 2 to 4 times a day.

| Ingredient | Weight | |
|---|---|---|
| | Tablet | Capsule |
| 1-methyl-4-butoxyquinolin-2(1H)-one | 50 | 50 |
| Tragacanth | 10 | — |
| Lactose | 197.5 | 250 |
| Cornstarch | 25 | |
| Talcum | 15 | |
| Magnesium stearate | 2.5 | |

The following examples are given for the purpose of illustration only:

EXAMPLE 1

1-Methyl-4-butoxyquinolin-2(1H)-one

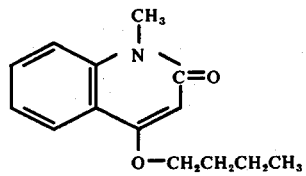

To a solution of 10.0 g. of 1-methyl-4-hydroxyquinolin-2(1H)-one in 150 ml. of dimethylformamide is added 2.4 g. of pentane washed with sodium hydride and the resulting mixture stirred for 2 hours at room temperature. There is then added 10.6 g. of n-butyl iodide and the resulting mixture is stirred for 24 hours at room temperature. The reaction mixture is then poured onto 1.3 liters of cold water, extracted with ethyl acetate, washed 3 times with water, dried, charcoaled, filtered and evaporated in vacuo. The resulting oil is dissolved in 120 ml. of ether and cooled in an acetone/dry ice bath to crystallize solids which are filtered off and washed with cold ether to obtain 1-methyl-4butoxyquinolin-2 (1H)-one, m.p. 77°–80° C.

EXAMPLE 2

Following the procedure of Example 1, the following additional compounds of the invention are prepared:
a. 1-methyl-4-hexoxyquinolin-2(1H)-one, m.p. 66–69° C.
b. 1-methyl-4-sec-butoxyquinolin-2(1H)-one, as an oil.
c. 1-methyl-4-isobutoxyquinolin-2(1H)-one, m.p. 85–87° C.
d. 1-methyl-4-pentoxyquinolin-2(1H)-one, m.p. 62–65° C.

What is claimed is:
1. A compound of the formula:

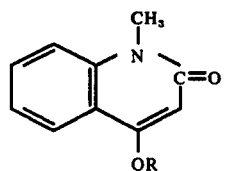

wherein R is alkyl of 4 to 6 carbon atoms.
2. A compound of claim 1 in which R is straight chain alkyl of 4 or 5 carbon atoms.
3. The compound of claim 2 which is 1-methyl-4-butoxyquinazolin-2(1H)-one.
4. The compound of claim 2 which is 1-methyl-4-pentoxyquinolin-2(1H)-one.